US009833221B2

(12) United States Patent
Hutchins et al.

(10) Patent No.: US 9,833,221 B2
(45) Date of Patent: Dec. 5, 2017

(54) APPARATUS AND METHOD OF IMAGE REGISTRATION

(71) Applicants: Christopher Hutchins, Londonderry, NH (US); Alexander Ship, Needham, MA (US)

(72) Inventors: Christopher Hutchins, Londonderry, NH (US); Alexander Ship, Needham, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 241 days.

(21) Appl. No.: 13/836,354

(22) Filed: Mar. 15, 2013

(65) Prior Publication Data

US 2014/0276020 A1  Sep. 18, 2014

(51) Int. Cl.
| | |
|---|---|
| *A61B 8/08* | (2006.01) |
| *A61B 8/12* | (2006.01) |
| *A61B 5/00* | (2006.01) |
| *A61B 8/00* | (2006.01) |

(52) U.S. Cl.
CPC .......... *A61B 8/5261* (2013.01); *A61B 5/0066* (2013.01); *A61B 5/0084* (2013.01); *A61B 8/12* (2013.01); *A61B 8/4416* (2013.01)

(58) Field of Classification Search
CPC ....... A61B 5/0066; A61B 5/0084; A61B 8/12; A61B 8/4416; A61B 8/5261
See application file for complete search history.

(56) References Cited

U.S. PATENT DOCUMENTS

| | | | |
|---|---|---|---|
| 5,076,279 A | 12/1991 | Arenson et al. | |
| 5,274,551 A | 12/1993 | Corby, Jr. | |

(Continued)

FOREIGN PATENT DOCUMENTS

| | | |
|---|---|---|
| JP | 11-056752 | 3/1999 |
| JP | 2002-153472 | 5/2002 |
| JP | 2004-290548 | 10/2004 |
| JP | 2006-006958 | 1/2006 |
| WO | 2008086613 | 7/2008 |
| WO | 2008086615 | 7/2008 |
| WO | 2008086616 | 7/2008 |

(Continued)

OTHER PUBLICATIONS

International Search Report and the Written Opinion of the International Searching Authority for International Application No. PCT/US2007/023493 dated Apr. 23, 2008.

(Continued)

*Primary Examiner* — Tse Chen
*Assistant Examiner* — Jason Ip
(74) *Attorney, Agent, or Firm* — K&L Gates LLP

(57) ABSTRACT

A method for bringing an IVUS and an OCT image into register. In one embodiment, the method includes obtaining an IVUS image of an area of a lumen; obtaining an OCT image of the same area of the lumen; determining the same asymmetry in each of the IVUS and OCT images; and overlaying the IVUS and OCT images and rotating them with respect to one another until the asymmetry in each of the IVUS and OCT images are in register, and determining the angle of rotation that resulted in the registration. In another aspect, the invention relates to a probe for OCT and IVUS imaging. In one embodiment, the probe includes a sheath having a first end and a second end defining a lumen; a marker that is opaque to light and ultrasound located between the first end and second end; and an IVUS/OCT probe head positioned within the sheath.

8 Claims, 7 Drawing Sheets

(56) References Cited

U.S. PATENT DOCUMENTS

| | | | |
|---|---|---|---|
| 5,293,873 A | 3/1994 | Fang |
| 5,313,949 A | 5/1994 | Yock |
| 5,321,501 A | 6/1994 | Swanson et al. |
| 5,335,662 A | 8/1994 | Kimura et al. |
| 5,350,377 A | 9/1994 | Winston et al. |
| 5,459,570 A | 10/1995 | Swanson et al. |
| 5,465,147 A | 11/1995 | Swanson |
| 5,509,093 A | 4/1996 | Miller et al. |
| 5,582,178 A | 12/1996 | Yock |
| 5,588,434 A | 12/1996 | Fujimoto |
| 5,619,368 A | 4/1997 | Swanson |
| 5,748,598 A | 5/1998 | Swanson et al. |
| 5,784,352 A | 7/1998 | Swanson et al. |
| 5,830,145 A | 11/1998 | Tenhoff |
| 5,956,355 A | 9/1999 | Swanson et al. |
| 6,111,645 A | 8/2000 | Tearney et al. |
| 6,129,667 A | 10/2000 | Dumoulin et al. |
| 6,134,003 A | 10/2000 | Tearney et al. |
| 6,160,826 A | 12/2000 | Swanson et al. |
| 6,191,862 B1 | 2/2001 | Swanson et al. |
| 6,217,527 B1 | 4/2001 | Selmon et al. |
| 6,226,546 B1 | 5/2001 | Evans |
| 6,265,792 B1 | 7/2001 | Granchukoff |
| 6,282,011 B1 | 8/2001 | Tearney et al. |
| 6,299,622 B1 | 10/2001 | Snow et al. |
| 6,302,875 B1* | 10/2001 | Makower et al. ............ 604/528 |
| 6,314,197 B1* | 11/2001 | Jain ................... G06K 9/00087 |
| | | | 382/125 |
| 6,421,164 B2 | 7/2002 | Tearney et al. |
| 6,423,002 B1 | 7/2002 | Hossack |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,585,660 B2 | 7/2003 | Dorando et al. |
| 6,706,004 B2 | 3/2004 | Tearney et al. |
| 6,847,454 B2 | 1/2005 | Crowley et al. |
| 6,879,851 B2 | 4/2005 | McNamara et al. |
| 6,891,984 B2 | 5/2005 | Petersen et al. |
| 6,947,787 B2 | 9/2005 | Webler |
| 7,134,994 B2 | 11/2006 | Alpert et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,366,562 B2 | 4/2008 | Dukesherer et al. |
| 7,397,935 B2 | 7/2008 | Kimmel et al. |
| 7,414,779 B2 | 8/2008 | Huber et al. |
| 7,415,049 B2 | 8/2008 | Flanders et al. |
| 7,477,763 B2 | 1/2009 | Willis et al. |
| 7,605,681 B2 | 10/2009 | Wobben |
| 7,621,874 B2 | 11/2009 | Romley et al. |
| 7,625,366 B2 | 12/2009 | Atlas |
| 7,729,745 B2 | 6/2010 | Maschke |
| 7,751,865 B2 | 7/2010 | Jascob et al. |
| 7,785,261 B2 | 8/2010 | Maschke |
| 7,813,609 B2 | 10/2010 | Petersen et al. |
| 7,818,044 B2 | 10/2010 | Dukesherer et al. |
| 7,822,464 B2 | 10/2010 | Maschke et al. |
| 7,840,253 B2 | 11/2010 | Tremblay et al. |
| 7,848,791 B2 | 12/2010 | Schmitt et al. |
| 7,916,387 B2 | 3/2011 | Schmitt et al. |
| 7,935,060 B2 | 5/2011 | Schmitt et al. |
| 8,162,834 B2 | 4/2012 | Feldman et al. |
| 8,214,010 B2 | 7/2012 | Courtney |
| 8,548,567 B2 | 10/2013 | Maschke |
| 2001/0031919 A1 | 10/2001 | Strommer et al. |
| 2002/0019644 A1 | 2/2002 | Hastings et al. |
| 2002/0049375 A1 | 4/2002 | Strommer et al. |
| 2002/0161351 A1 | 10/2002 | Samson et al. |
| 2005/0025797 A1 | 2/2005 | Wang et al. |
| 2005/0043614 A1* | 2/2005 | Huizenga et al. ............ 600/427 |
| 2005/0101859 A1 | 5/2005 | Maschke |
| 2005/0113685 A1 | 5/2005 | Maschke et al. |
| 2005/0149002 A1 | 7/2005 | Wang et al. |
| 2005/0201662 A1 | 9/2005 | Petersen et al. |
| 2006/0025677 A1 | 2/2006 | Verard et al. |
| 2006/0084867 A1 | 4/2006 | Tremblay et al. |
| 2006/0095065 A1 | 5/2006 | Tanimura et al. |
| 2006/0100489 A1 | 5/2006 | Pesach et al. |
| 2006/0116577 A1 | 6/2006 | DeWitt |
| 2006/0173299 A1 | 8/2006 | Romley et al. |
| 2006/0241465 A1* | 10/2006 | Huennekens et al. ........ 600/458 |
| 2006/0241572 A1 | 10/2006 | Zhou |
| 2007/0038061 A1 | 2/2007 | Huennekens et al. |
| 2007/0060822 A1 | 3/2007 | Alpert et al. |
| 2007/0135803 A1* | 6/2007 | Belson ............................. 606/1 |
| 2007/0232933 A1 | 10/2007 | Gille et al. |
| 2007/0243137 A1 | 10/2007 | Hainfeld |
| 2008/0161696 A1 | 7/2008 | Schmitt et al. |
| 2008/0171937 A1 | 7/2008 | Dukesherer et al. |
| 2008/0177139 A1 | 7/2008 | Courtney et al. |
| 2008/0177183 A1 | 7/2008 | Courtney et al. |
| 2008/0180683 A1 | 7/2008 | Kemp |
| 2008/0269572 A1 | 10/2008 | Kanz et al. |
| 2008/0287795 A1 | 11/2008 | Klingensmith et al. |
| 2009/0018393 A1 | 1/2009 | Dick et al. |
| 2009/0043191 A1 | 2/2009 | Castella et al. |
| 2009/0174931 A1 | 7/2009 | Huber et al. |
| 2009/0195514 A1 | 8/2009 | Glynn et al. |
| 2009/0264768 A1 | 10/2009 | Courtney et al. |
| 2009/0299195 A1 | 12/2009 | Muller et al. |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0210939 A1 | 8/2010 | Hartmann et al. |
| 2010/0253949 A1 | 10/2010 | Adler et al. |
| 2010/0274124 A1 | 10/2010 | Jascob et al. |
| 2011/0007315 A1 | 1/2011 | Petersen et al. |
| 2011/0058178 A1 | 3/2011 | Tearney et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2012/0057157 A1 | 3/2012 | Petersen et al. |
| 2012/0116214 A1 | 5/2012 | Muller et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0310081 A1 | 12/2012 | Adler et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |

FOREIGN PATENT DOCUMENTS

| | | |
|---|---|---|
| WO | 2009009802 | 1/2009 |
| WO | 2009137659 | 11/2009 |
| WO | 2013 116305 A1 | 8/2013 |

OTHER PUBLICATIONS

Partial European Search Report for European Application No. 14156269.4 mailed from the European Patent Office dated Oct. 27, 2014 (6 pages).

Fornell, "The Advantages and Disadvantages of OCT vs. IVUS," May 18, 2011, Diacardiology.com, pp. 1-4.

* cited by examiner

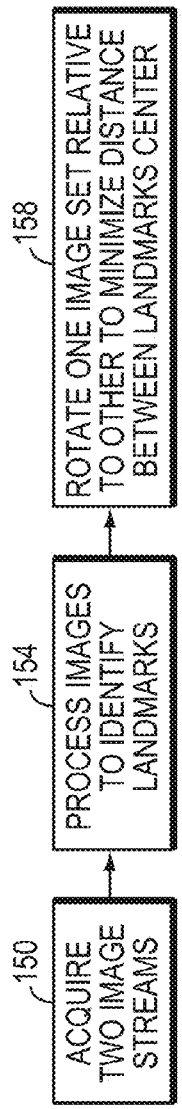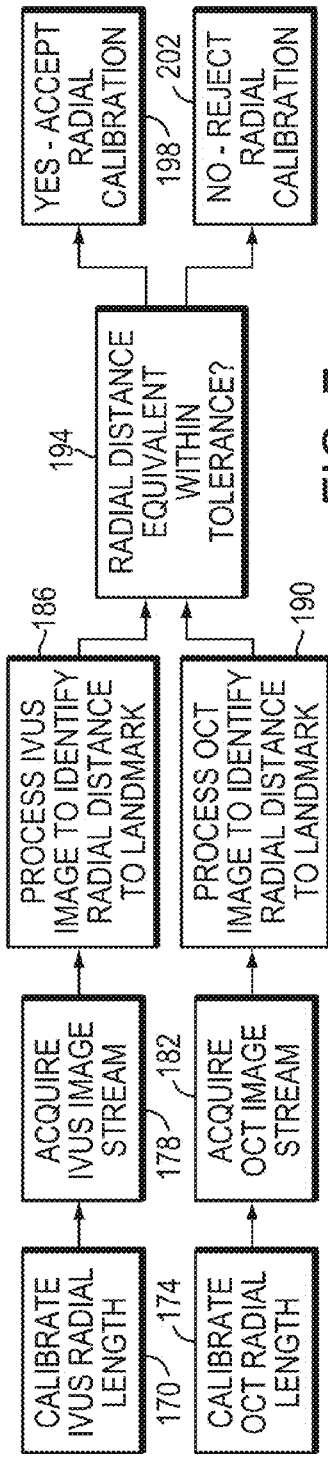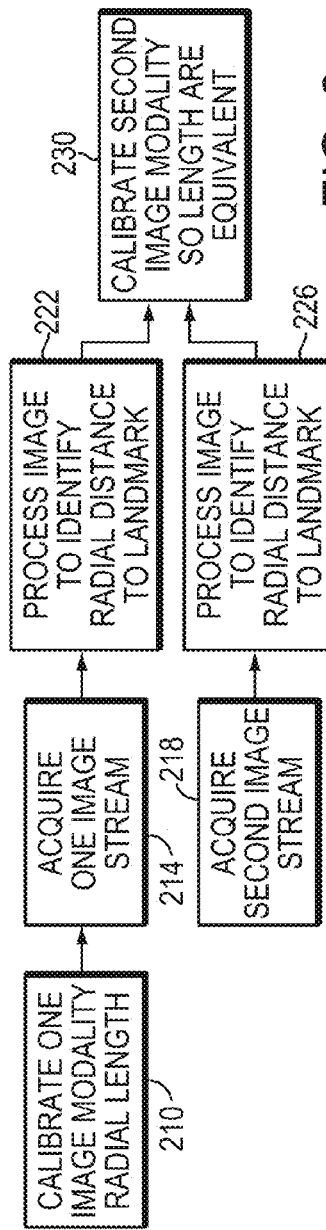
FIG. 6
FIG. 7
FIG. 8

APPARATUS AND METHOD OF IMAGE REGISTRATION

FIELD OF THE INVENTION

The invention relates generally to the field of medical imaging and more specifically to the field of Optical Coherent Tomography (OCT) and IntraVascular UltraSound (IVUS) imaging.

BACKGROUND OF THE INVENTION

OCT interferometric methods deliver light onto a sample of interest, such as the wall of a lumen of a blood vessel, and collect a portion of the light returned from the sample. Due to the size and complexity of many light sources and light analysis devices, the sources and light detectors are typically located remotely from the sample area of interest. One method of optically analyzing internal parts is to guide light from a remote light source onto the sample using a thin optical fiber that is minimally disruptive to the normal function of the sample. This minimal disruption occurs because of the diminutive cross-section of the optical fiber.

There are many miniature optical systems known in the art that can be used for analysis of internal lumen structures. Each optical system can be conceptually divided into a beam delivery and focusing means, and a beam directing means. Light is passed from an external light source to the internal lumen through one or more optical illumination fibers, which may be single mode or multimode in nature. The illumination fiber is in communication with the miniature optical system, which focuses and directs the beam into the luminal wall.

Light is reflected by the lumen wall and transmitted to an analysis apparatus outside the body, generally using the same fiber as transmitted the incident light. The analysis apparatus is typically interferometric and the resulting interferometric patterns are detected and transformed into an image by a computer. In use, the fiber spins within the lumen of the vessel, thereby sweeping the wall with the light and collecting the reflected light. Each revolution of the fiber therefore produces a scanned cross-sectional image of the vessel. As the fiber is retracted or pulled out of the vessel, a cylindrical image of a portion of the vessel lumen is obtained.

An IVUS probe is similar to an OCT probe; however, the IVUS probe uses ultrasound rather than light. Ultrasonic pulses are produced by an IVUS transducer at the probe tip and the sound reflected by the walls of the lumen is received by the transducer and converted into electrical signals which are then analyzed by a computer. As with OCT imaging, the IVUS probe spins in the lumen of the vessel and this results in a reflection pattern from the walls of the vessel that is also analyzable by computer to produce a cross-sectional image. Again, as the IVUS probe is withdrawn from the vessel, a cylindrical image of a portion of the vessel lumen is obtained.

Now that combination OCT and IVUS probes have become available, it is possible to acquire both images in one procedure. Obtaining both of the IVUS and OCT images of the vessel has benefits, because of the inherent advantages and limitations of each imaging modality. OCT light tends to be scattered by particles, such as blood cells passing through the lumen of the vessel. This scattering degrades the resulting OCT image of the vessel wall. However, OCT light penetrates into the wall of the vessel thereby being able not only to image the wall of the vessel but also the intima of the vessel. IVUS ultrasonic pulses are not as affected by particles in the lumen. Therefore, IVUS and OCT images can complement one another.

Because the two images, whether taken with the same probe or different probes, have different resolution, the alignment of the images to form a usable composite image is difficult. In addition, because of other limitations that will be discussed below, accurate determination of actual distances in the images is difficult. What is needed is a way to process the OCT and IVUS images so that both images depict the same region of the vessel, at the same magnification and orientation, and with a mechanism to check the calibration of each imaging modality.

The present invention addresses this need.

SUMMARY OF THE INVENTION

In one aspect, the invention relates to a probe for OCT and IVUS imaging. In one embodiment, the probe includes a sheath having a first end and a second end, and a wall defining a lumen; a marker that is opaque to light and ultrasound and is located between the first end and second end of the sheath; and an IVUS/OCT probe head positioned within the sheath. In another embodiment, the marker is a cylindrical annular device positioned on the outside wall of the sheath. In yet another embodiment, the marker is a cylindrical annular device positioned on the inside wall of the sheath. In still another embodiment, the marker is a cylindrical annular device positioned within the wall of the sheath. In still yet another embodiment, the marker is a bar positioned on the outside wall of the sheath. In yet another embodiment, the marker is a bar positioned on the inside wall of the sheath. In still yet another embodiment, the marker is a bar positioned within the wall of the sheath.

In another embodiment, the system includes a probe for OCT and IVUS imaging that includes a sheath having a first end and a second end and a wall defining a lumen; a marker that is opaque to light and ultrasound and is located between the first end and second end of the sheath; and an IVUS/OCT probe head positioned within the sheath; and an analysis and instrumentation unit in communication with the probe; and a display in communication with the analysis and instrumentation unit. In another embodiment, the processor of the analysis and instrumentation unit is configured to locate the marker in each of an OCT image and an IVUS image, and rotates at least one of the OCT image and IVUS image until the marker in both images is in register. In yet another embodiment, the system includes a probe for OCT and IVUS imaging; an analysis and instrumentation unit in communication with the probe; and a display in communication with the analysis and instrumentation unit. In still yet another embodiment, the processor is configured to locate the same symmetry in each of an OCT image and an IVUS image, and rotate at least one of the OCT image and IVUS image until the asymmetry in both images is in register.

In one embodiment, the asymmetry in the OCT image and the IVUS image is caused by a guidewire. In another embodiment, the asymmetry in the OCT image and the IVUS image is caused by the shape of the lumen being imaged. In yet another embodiment, the asymmetry in the OCT image and the IVUS image is caused by the internal morphology of the lumen.

In another aspect, the invention relates to a method of bringing an IVUS image and an OCT image into register. In one embodiment, the method includes obtaining an IVUS image of an area of a lumen; obtaining an OCT image of the same area of the lumen; determining the same asymmetry in each of the IVUS and OCT images; and overlaying the IVUS and OCT images and rotating them with respect to one another until the asymmetry in each of the IVUS and OCT images are in register, and determining the angle of rotation that resulted in the registration. In another embodiment, the asymmetry in the OCT image and the IVUS image is caused by a guidewire. In yet another embodiment, the asymmetry in the OCT image and the IVUS image is caused by the shape of the lumen being imaged. In still yet another embodiment, the asymmetry in the OCT image and the IVUS image is caused by the internal morphology of the lumen. In one embodiment, the method includes obtaining an IVUS image of an area of a lumen having a marker; obtaining an OCT image of the same area of the lumen having the marker; determining the orientation of the marker in each of the IVUS and OCT images; and overlaying the IVUS and OCT images and rotating them with respect to one another until the marker in each of the IVUS and OCT images are in register, and determining the angle of rotation that resulted in the registration.

In another aspect, the invention relates to a method of checking the calibration of an OCT system. In one embodiment, the system includes a probe having a probe head in a sheath having a reflector. In another embodiment, the method uses an IVUS system having an ultrasonic transducer on the probe head. In yet another embodiment, the method includes the steps of measuring the amount of time it takes for the ultrasonic pulse to leave and return to the IVUS transducer; calibrating the OCT system by measuring the distance to the known reflector in the sheath; acquiring an IVUS image and an OCT image of a vessel comprising a wall defining a lumen; processing each image to measure the distance from the probe location in the lumen to the wall in the vessel; and comparing the OCT distance measurement with the IVUS distance measurement to determine if the two measurements are equivalent to within a predetermined value.

Another aspect of the invention relates to a method for determining the identity of the fluid being used as a flushing fluid in a vessel having a wall having a landmark, the wall defining a lumen. In one embodiment, the method includes the steps of measuring the distance to a landmark on the wall of the vessel from a probe head using OCT; measuring the round-trip time it takes for the IVUS ultrasonic pulse to reach the same landmark and return; dividing the OCT measured distance by half the IVUS measured round-trip time to obtain a measured speed of sound in the fluid; and comparing the measured speed of sound in the fluid to the speed of sound in various flushing solutions.

Another aspect of the invention relates to a method of characterizing a tissue. In one embodiment, the method includes the steps of measuring, using OCT, the distance to an edge of the tissue; measuring, using OCT, the distance to another landmark within the tissue; subtracting the distance to the edge of the tissue from the distance to the landmark in the tissue to determine a thickness of the tissue between the tissue edge and the landmark; measuring the time it takes for an IVUS acoustic pulse to reach the same edge of the tissue; measuring the time it takes for the IVUS acoustic pulse to reach the landmark; subtracting the time it takes the IVUS acoustic pulse to reach the edge of the tissue from the time it takes the IVUS acoustic pulse to reach landmark to calculate the transit time through the tissue to the landmark; dividing the thickness of the tissue measured by OCT by the transit time measured by IVUS, to determine the measured speed of sound in the tissue; and comparing the measured speed of sound in the tissue to the speed of sound in various tissues to determine the tissue characteristic.

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

FIG. 6 is a flow diagram of an embodiment of a method for rotational alignment;

FIG. 7 is a flow diagram of an embodiment of a method for radial calibration and alignment;

FIG. 8 is a flow diagram of another embodiment of a method for radial calibration and alignment.

DETAILED DESCRIPTION

The issue of calibration and alignment of an IVUS and an OCT image occurs whether the IVUS and OCT components are located on the same probe or different probes. Even if the IVUS and OCT transducers are in the same probe, actual manufacturing tolerances permit sufficient deviation in the direction of the beam emitting from each of the OCT and IVUS components that the beams are not parallel.

Figure 1:
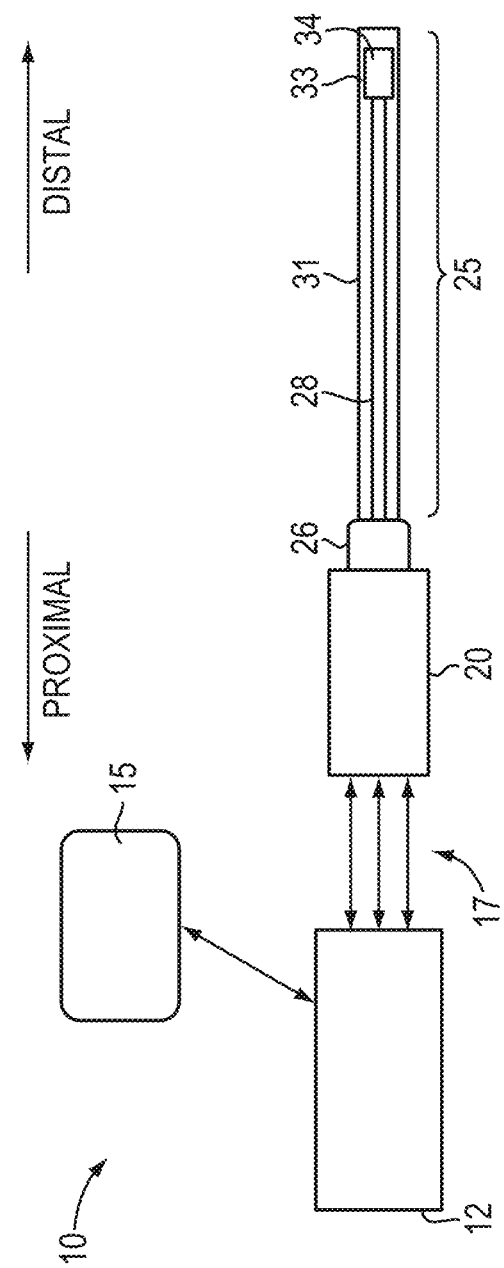
FIG. 1 is a block diagram of an embodiment of an OCT/IVUS system.

Referring to FIG. 1, a combination IVUS and OCT system 10 is shown in block diagram. The system 10 includes an analysis and instrumentation unit (AIU) 12, which includes a processor and an interferometer for use with the OCT optics of the probe, and an ultrasound generator for use with the IVUS transducer of the probe. The analysis and instrumentation unit 12 is in communication with a display 15. The analysis and instrumentation unit 12 is connected by electrical conductors and optical fibers 17 to a patient interface unit (PIU) 20. The PIU 20 includes the motors, optical and electrical connections necessary to rotate, translate, and provide current and light to the probe 25. The probe 25 is removably coupled to the PIU 20 by way of a removable electrical/optical coupler 26. The probe itself includes an optical fiber/electrical conductor combination 28 within a sheath 31. The optical fiber/electrical conductor combination 28 connects to the OCT optics 33 and the IVUS transducer 34.

Figure 2B:
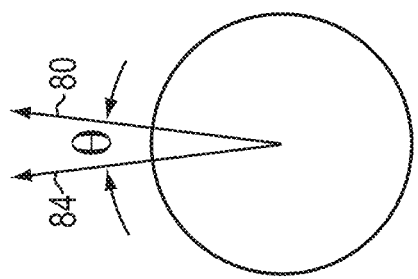
FIG. 2(b) is a diagram of the angular divergence of the ultrasonic and light beams of the probe head of FIG. 2(a)
Figure 2A:
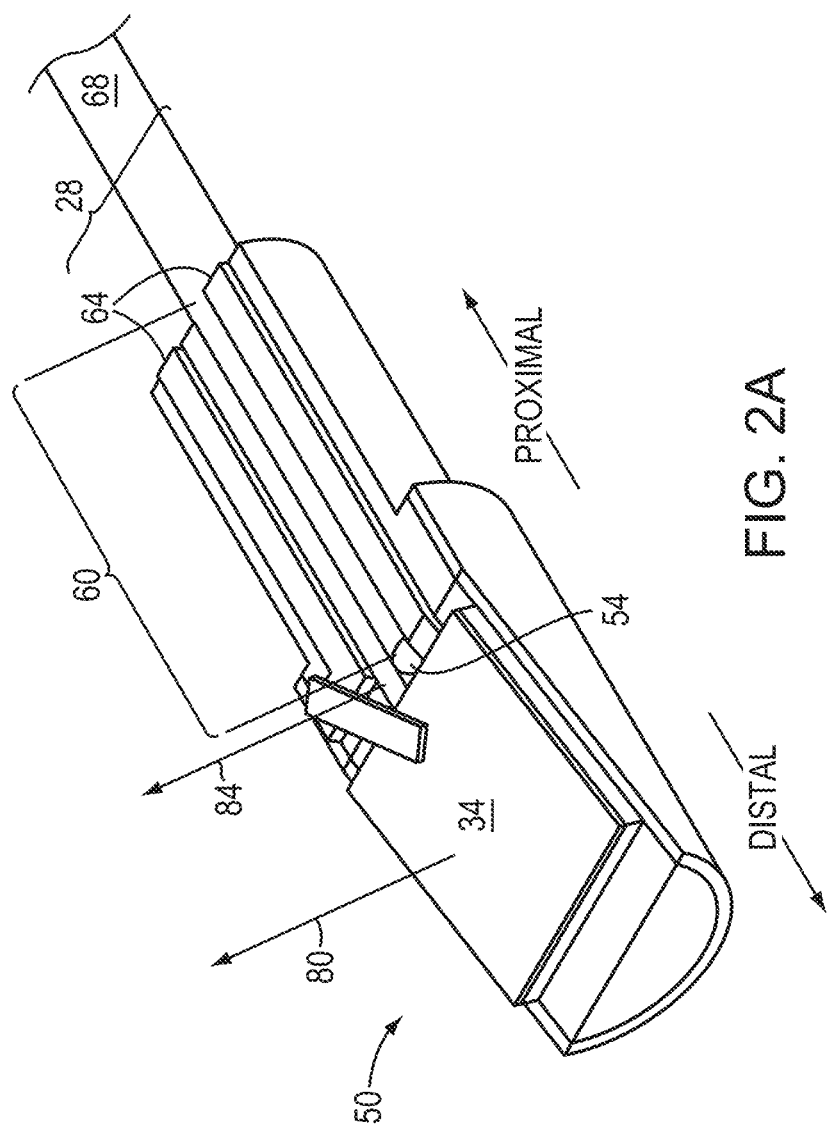
FIG. 2(a) is a schematic diagram of an embodiment of the IVUS and OCT head of the probe of FIG. 1.

In more detail and referring to FIG. 2(a), a view of the OCT/IVUS head 50 of the probe 25 includes an ultrasonic transducer 34 and an optical beam director 52 that is part of the optical train (lenses, collimator, etc) 60 of the OCT optics. As stated above, the electrical conductors 64 and optical fiber 68 form the optical fiber/electrical conductor combination 28.

The ultrasonic transducer 34 generates an ultrasonic beam 80 perpendicular to the surface of the transducer 34. Similarly, the beam director 52 directs light along a beam 84 substantially parallel to the ultrasonic beam 80. The two beams, ultrasonic and light should be directed in parallel but due to manufacturing limitations the may deviate by a few degrees ($\theta$). The result is that the IVUS image of the vessel and the OCT image of the vessel may be rotated ($\theta$) degrees with respect to one another (FIG. 2B).

Figure 3:
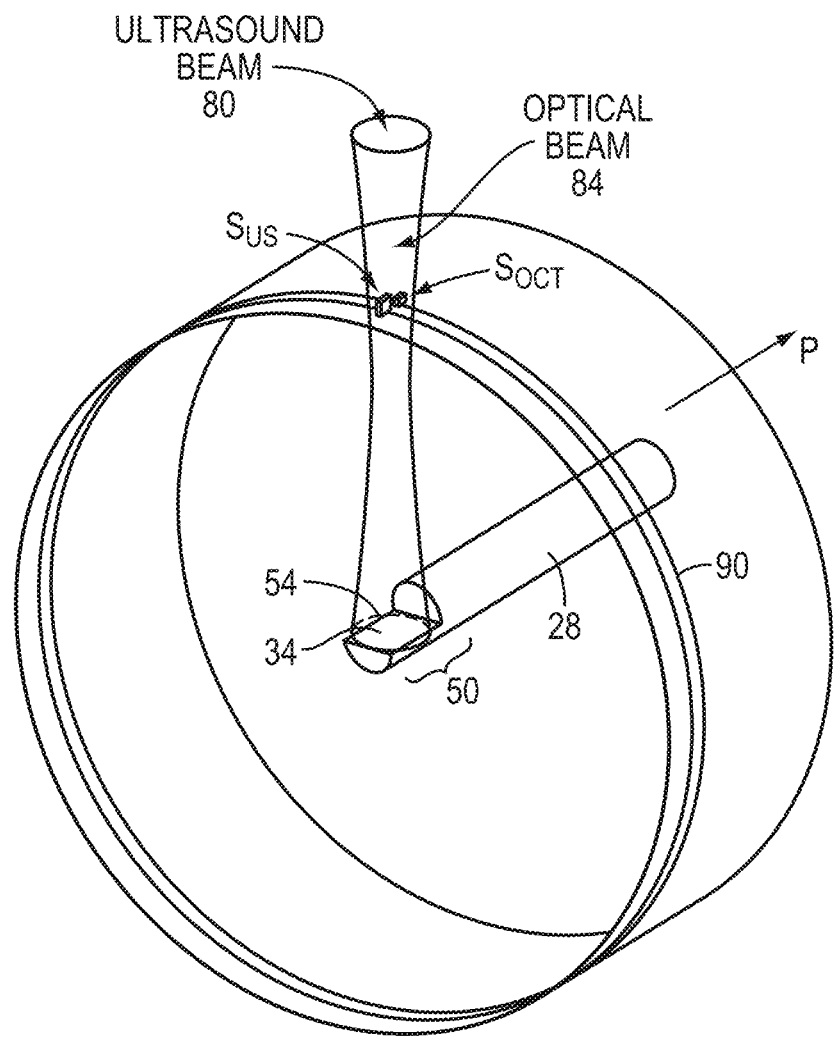
FIG. 3 is a highly schematic diagram of an embodiment of the ultrasonic and light beams of the probe head of FIG. 2(a) sweeping out a volume of space.

Referring to FIG. 3, as the head of the probe 50 spins and is withdrawn from the vessel, the path 90 of the optical beam 84 and ultrasound beam 80 against the vessel wall is in the form of a spiral. In the embodiment shown, the IVUS transducer 34 is further forward in the probe head than the beam director 54, so that as the probe head 50 is withdrawn from the vessel (directional arrow P), the OCT beam 84 images an area of the vessel ($S_{OCT}$) several revolutions of the head 50 earlier than the ultrasound beam 80 images substantially the same the area ($S_{US}$). Thus, to image the same portion of the vessel wall, the software of the system must take into account the delay caused by the difference in placement of the IVUS transducer 34 and the beam director 54 in the head of the probe 50. However, even when this delay is accounted for, the IVUS image and the OCT image may be rotated with respect to one another as described above.

In one embodiment, one way to address this radial offset ($\theta$) is to measure the offset accurately after manufacture. This may be accomplished by placing the probe head into a cylindrical fixture having known patterns on the walls of its lumen. Next the probe head is withdrawn and IVUS and OCT images are captured. Because the actual features are known, the images taken with OCT and IVUS can then be co-registered. By counting the number of frames between the OCT image of an area of wall and the IVUS image of the same area of wall, the delay between images can be determined. By noting how many degrees of rotation are needed to align the images, ($\theta$) can be determined. This information may be encoded into a bar code or equivalent or an RFID tag attached to the probe connector 20 (FIG. 1). The user of the system 10 can then program this information into the system using a bar code reader or RFID reader so that the IVUS and OCT images are displayed together with the same orientation and magnification.

Figures 4B, 4C:
FIG. 4(b) is an end view of the discontinuous fiducial marker of FIG. 4(a)
FIG. 4(c) is an end view of the bar fiducial marker of FIG. 4(a)
Figure 4A:
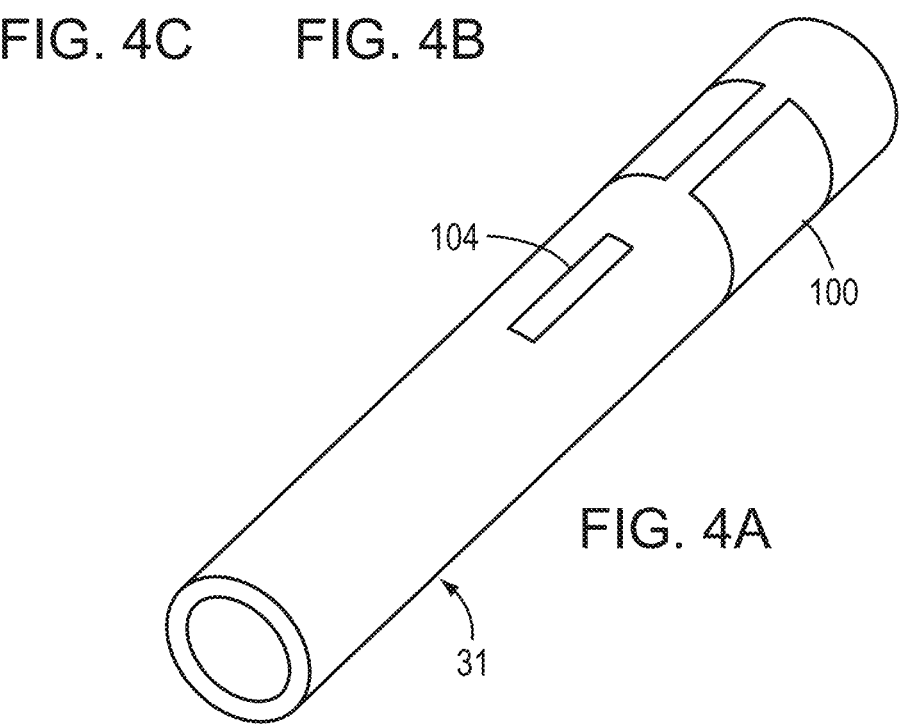
FIG. 4(a) is a diagram of an embodiment of a probe with a discontinuous fiducial marker and a bar fiducial marker.

Alternatively, the system can self-calibrate using one of several imaging techniques. In one embodiment, referring to FIG. 4(a), the sheath 31 (FIG. 1) is manufactured with a discontinuous cylindrical annulus 100 attached to the outside wall or inside wall of the sheath 31. In FIG. 4(b), an end-on view of the annulus 100' is shown. Alternatively, the sheath may have a fiducial bar 104, shown end-on in FIG. 4(c). In both cases, the fiducial bar 104 and discontinuous cylindrical annulus 100, collectively referred to as a fiducial marker, provide an asymmetry in the image which is detectable by both OCT and IVUS imaging. Note that the fiducial bar 104 and the discontinuous fiducial annulus 100 are not used together on the same sheath 31, and are shown together only to provide positioning information. The fiducial marker may be made of any optically opaque material that has a different optical density and acoustic attenuation than the sheath 31. The fiducial marker may be positioned anywhere along the sheath 31, but generally near one end of the region through which the probe head must pass during pull back.

Figure 4D:
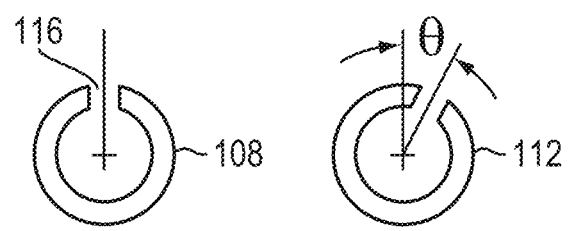
FIG. 4(d) is an image view of the discontinuous fiducial marker of FIG. 4(a) taken by IVUS and OCT.

The ends of the pull-back are typically used to position the fiducial marker in order to make sure the imaging of the regions of interest in the vessel wall are not blocked by the fiducial marker. FIG. 4(d) shows an image 108 of the marker 100 as seen by one modality, and the same image as seen by the other modality 112. The difference in orientation between the split in the discontinuous annulus 116 taken by one modality, such as IVUS, and the image of the split taken by the other modality (112), such as OCT, is the angle ($\theta$). The system 10 can then determine how much to rotate the images 112, 116 so as to have the IVUS and OCT images coincide.

Figure 5:
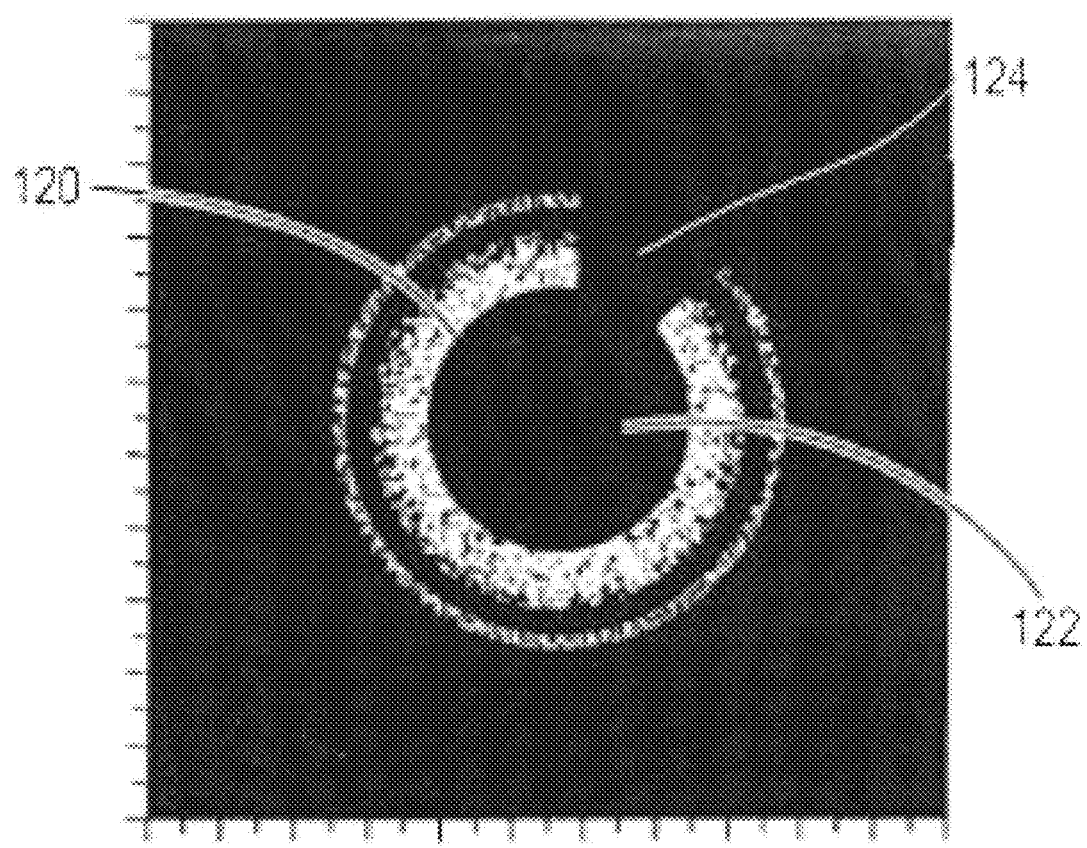
FIG. 5 is an OCT image of a vessel with a guidewire shadow.

Another embodiment by which the system 10 can self-calibrate is by identifying asymmetries in the images recorded by both the IVUS and the OCT modalities. One asymmetry that may be used is caused by a guidewire which the probe follows to its location in the blood vessel. Referring to FIG. 5, in this OCT image of a blood vessel, the wall of the vessel 120 appears as a light boundary surrounding the black lumen 122 of the vessel. The guide wire passes through the lumen and is opaque to the light from the OCT probe. As a result, the guidewire appears to be a break or shadow 124 across the lumen boundary wall 120.

In one embodiment, the same software that determines if this form of shadow is a guidewire or a vessel branch in general OCT imaging applications is used to determine the orientation of the image by finding the center point of the shadow. A discontinuity in the image of the vessel wall caused by the guidewire also appears in an IVUS image because the guidewire is opaque to the ultrasonic beam. Thus, by using the discontinuity caused by the guidewire, one can again rotate the images until the guidewire discontinuities are aligned in both modalities.

In another embodiment, the same procedure can be used with asymmetries in the vessel wall itself. For example, an image of a vessel cross-section may show that the vessel is not circular but is some other shape, such as ellipsoidal, that is not a 360° symmetrical shape. In this case, both OCT and IVUS image generating programs are capable of finding the major and minor axes of the cross-section. Once these axes are found, one image is rotated until the major and minor axes of the images of both modalities are in register. This technique can also be done using some other asymmetry in the vessel cross-sectional image, for example the presence of plaque. However, identifying a specific plaque lesion by one or the other modality may be difficult.

In more detail, in one embodiment, the OCT and IVUS images are aligned by rotationally transforming one helical image set relative to the other based upon the time delay between the ultrasound and optical imaging beams. That is, given that OCT systems and ultrasound systems have different resolution ranges and depths of penetration, it is desirable to display a fused image or overlaid image of the lumen that includes both OCT data and ultrasound data. To do this with an axially displaced pair of acoustic and optical sensors in the probe tip requires a rotational transformation of the acquired data sets so that images of the same anatomic locations (acquired at offset times) are registered over each other as discussed above. Once the images are rotationally transformed, the two images can be fused together. A number of different techniques can be used to combine portions of images, or otherwise generate new images, from some or all of an IVUS image and an OCT image generated using one of the embodiments described herein.

Referring to FIG. 6, a generalized flow chart of the method for rotationally aligning two images is shown. The two images to be aligned are acquired 150, and landmarks, as discussed above, are identified 154. The magnification for the two images is equalized. The images are then rotated until the distance between the same point of the landmark in both images is minimized 158.

In addition to rotational registration, the combination of IVUS and OCT provides additional data that is useful in determining magnification, confirming calibration, confirming the nature of the flush solution, and determining tissue characteristics.

Distance measurements using OCT are difficult. Generally, this difficulty arises because the measurement of distance using interference fringes is affected by the relative lengths of the measurement arm and the reference arm of the interferometer. The measurement arm of the interferometer includes the length of the fiber in the probe itself, and the length of the fiber connecting the probe to the interferometer. This means that small distance measurements within a vessel are a very small part in what is a very long measurement arm. The fiber in the probe is substantially at the temperature of the fluid used to flush blood from the vessel, while portions of the rest of the fiber measurement arm that are not in contact with the flush fluid may be at a different temperatures. Because these temperatures may vary over time, the lengths of the various fiber portions exposed to different changing temperatures will change differentially from one another, causing the interference fringes to shift. The resulting error in the measurement of distance in the lumen is therefore large.

One attempt to address this error is to put a known reflector in the light path at an approximately known distance from the probe head. This reflector is generally placed on the sheath that surrounds the optical fiber. This reflector provides an approximate distance value that may then be used to calibrate distances in the OCT image. However, because the head position within the sheath and within the lumen moves as the head rotates, and because of the temperature variations, a second method of checking the calibration of the OCT system is desired. The IVUS portion of the probe is used for this purpose.

Because the time it takes for an ultrasonic pulse to move from the transducer and return to the transducer after reflecting from the wall of the vessel can be measured very accurately, and because the speed of sound in the flush solution is known, the distance to the surface of the wall is accurately known. Therefore, by comparing the distance to the wall as measured by OCT and the distance to the wall as measured by IVUS, the accuracy of the calibration of the OCT portion of the device may be determined.

Referring to FIG. 7, to determine if the calibration of the OCT system is accurate, one first calibrates the IVUS system by measuring the amount of time it takes for the ultrasonic pulse to leave and return to the transducer 170 and calibrates the OCT system by measuring the distance to a known reflector in the sheath 174. Next, an IVUS image 178 and an OCT image 182 of the vessel are acquired. Each image is processed (186 for IVUS and 190 for OCT) to measure the distance from the center probe location in the lumen to the wall in the vessel. The two distance measurements (OCT and IVUS) are compared 194 to determine if they are equivalent to within a predetermined value. If they are, the calibration is deemed accurate 198 and their relative magnifications are known. If they are not, the systems must be recalibrated 202.

Referring to FIG. 8, another embodiment of a method to calibrate an IVUS and an OCT system is to calibrate 210 one of the modalities IVUS or OCT (typically the IVUS portion) and then acquire an image of the vessel with that modality 214. An image is acquired with the other modality 218 and each image is processed 222, 226 to measure the distance from the center of the probe location in the lumen to a landmark, such as a wall. The two distance measurements are compared 230 to determine if they are equivalent to within a predetermined value and if they are not, the uncalibrated modality is adjusted until the lengths are equivalent.

In addition to calibration, the combined modalities are useful in confirming the identity of the fluid being used as a flushing fluid. To do this, the distance to a landmark on the wall of the vessel is measured using OCT. The time it takes for the IVUS ultrasonic pulse to reach the same landmark and return is also measured. By dividing the OCT measured distance by half the IVUS measured round-trip time, the speed of sound in the fluid is calculated. By looking up the speed of sound in the various possible flushing solutions, one can determine which solution is being used. If the solution as determined by the method is different from the solution name entered into the system by the clinician during the setup of the imaging procedure, an alarm may be given that the wrong fluid is being used and hence the measurements may not be correct.

Figure 9:
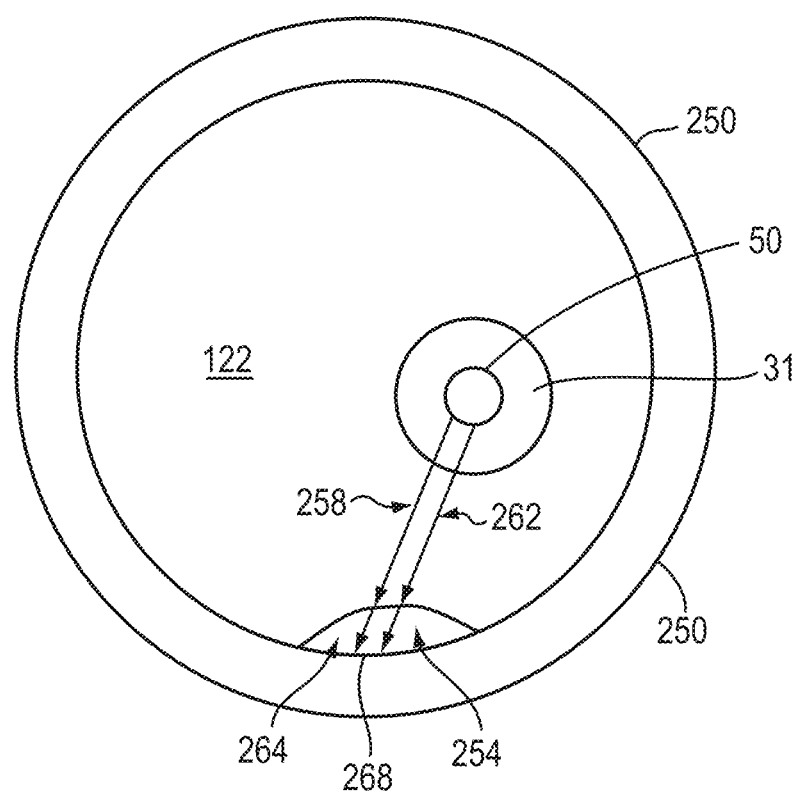
FIG. 9 is a diagram of an embodiment of the components of measurement of tissue characteristics using IVUS and OCT.

Finally, referring to FIG. 9, a probe head 50 is shown within a sheath 31 within the lumen 122 of a vessel 250. A lesion 254 on the wall 250 is subjected to the OCT light beam 258 and the IVUS acoustic beam 262. The OCT beam 258 measures the distance to the surface 264 of the lesion 254 and the distance to another landmark 268 inside the lesion 254. From these two measurements, the thickness of the lesion 254 between its surface 264 and the landmark 268 is determined. The time it takes for the IVUS acoustic pulse to reach the same surface 264 of the lesion and the time it takes for the acoustic pulse to reach the landmark 268 is also measured. By subtracting the two times, the transit time through the lesion is calculated. By dividing the thickness of the lesion measured by OCT by one half of the transit time, measured by IVUS, the speed of sound in the lesion is determined. Because different lesions are characterized by different speeds of sound, the type of lesion can then be determined.

In one embodiment, the OCT and IVUS image data can be combined by displaying OCT data for a specific depth of the image and then limiting the rest of the data displayed after that depth to IVUS data. This approach can be modified such that the OCT data is displayed until the depth where the OCT signal can no longer be discerned above the noise floor is reached, and then the remainder of the image is filled in with the deeper penetrating IVUS image data.

More sophisticated image data combination is also possible if each sample is a weighted combination of the IVUS and OCT grayscale adjusted for sample depth, and grayscale of adjacent samples. In one embodiment, each of the IVUS data set and the OCT data set includes a respective grayscale for each sample and depth information for each sample. In one embodiment, the method includes the step of generating a combined grayscale for each sample in an image generated using the OCT data set and the IVUS data. The combined grayscale is based on the grayscale of the IVUS dataset and the grayscale of the OCT dataset in the sample and the surrounding samples, as well as the depth of that sample.

Additionally, identification of the tissue type may be possible by contrasting the differential absorption of the IVUS and OCT energy by a sample. That is, tissue that is reflective in one domain (OCT) may be transmissive in the other domain (IVUS). Thus, it is possible to highlight a region as a calcium plaque or lipid plaque based on differences in transmission.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of registering an intravascular ultrasound (IVUS) image and an optical coherence tomography (OCT) image comprising:
    obtaining a first helical image data set, using a combination IVUS and OCT system, the first helical image data set comprising IVUS data of a blood vessel having a lumen, the IVUS data collected with an intravascular probe;
    obtaining a second helical image data set, using the combination IVUS and OCT system, the second helical image data set comprising OCT data of the blood vessel, the OCT data collected with the intravascular probe;
    generating an IVUS image and an OCT image from the IVUS data and the OCT data, respectively;
    detecting an asymmetry in the OCT data and the IVUS data using a software application of the combination IVUS and OCT system, wherein the asymmetry is a cylindrical annulus marker, wherein the marker defines a gap in the annulus;
    overlaying the IVUS image and the OCT images and rotating them with respect to one another, using the software application, until the asymmetry in each of the IVUS and OCT images are in register, and
    determining an angle of rotation that resulted in the IVUS image and the OCT image being in register.

2. The method of claim 1 wherein the asymmetry in the OCT image and the IVUS image is further caused by a shape of the lumen being imaged.

3. The method of claim 1 wherein the asymmetry in the OCT image and the IVUS image is further caused by an internal morphology of the lumen.

4. A method of registering intravascular ultrasound (IVUS) image data and an optical coherence tomography (OCT) image data comprising:
    obtaining an IVUS image of an area of a blood vessel having a lumen using ultrasound data collected with a rotatable intravascular probe comprising a sheath and a marker that is opaque to light and ultrasound,
    the marker comprising a cylindrical annulus, the cylindrical annulus having a gap defined thereby, the cylindrical annulus disposed on or in the sheath;
    obtaining an OCT image of the area of the lumen using optical data collected with the rotatable intravascular probe;
    imaging the gap of the cylindrical annulus;
    determining an orientation of the marker in each of the IVUS and OCT images by imaging the gap in the cylindrical annulus;

overlaying the IVUS and OCT images and rotating them with respect to one another until the gap in each of the IVUS and OCT images is in register with the other; and
determining an angle of rotation that resulted in the IVUS image and the OCT image being in register.

5. The method of claim 4, comprising positioning the rotatable intravascular probe in the lumen such that the marker is located in a region that will be imaged thereby.

6. The method of claim 4, further comprising registering additional IVUS images and OCT images based on the angle of rotation.

7. The method of claim 1 further comprising rotationally transforming the first helical image data set relative to the second helical image data set based upon the time delay between the ultrasound and optical imaging beams.

8. The method of claim 1 further comprising registering additional IVUS images and OCT images based on the angle of rotation.

* * * * *